(12) United States Patent
Muller-Feuga

(10) Patent No.: US 6,492,149 B1
(45) Date of Patent: Dec. 10, 2002

(54) METHOD FOR IMPROVING THE PERFORMANCE OF A PHOTOBIOREACTOR

(75) Inventor: Arnaud Muller-Feuga, Nantes (FR)

(73) Assignee: Institut Francais de Recherche pour l'Exploitation de la Mer, Issy les Moulineaux (FR)

( * ) Notice: Subject to any disclaimer, the term of this patent is extended or adjusted under 35 U.S.C. 154(b) by 0 days.

(21) Appl. No.: 09/807,666

(22) PCT Filed: Oct. 19, 1998

(86) PCT No.: PCT/FR98/02234

§ 371 (c)(1),
(2), (4) Date: Apr. 17, 2001

(87) PCT Pub. No.: WO00/23562

PCT Pub. Date: Apr. 27, 2000

(51) Int. Cl.⁷ .......................... C12N 13/00; C12N 1/12; C12M 1/00; C12M 3/00
(52) U.S. Cl. ................................ 435/173.8; 435/257.1; 435/292.1
(58) Field of Search ............................... 435/292.1, 420, 435/260, 173.8, 257.1

(56) References Cited

U.S. PATENT DOCUMENTS

| 4,868,123 A | * | 9/1989 | Berson et al. |
| 5,137,828 A | * | 8/1992 | Robinson et al. |
| 5,589,935 A | * | 12/1996 | Biard |
| 5,614,378 A | * | 3/1997 | Yang et al. |

FOREIGN PATENT DOCUMENTS

FR 2576034 * 7/1986

* cited by examiner

*Primary Examiner*—Christopher R. Tate
(74) *Attorney, Agent, or Firm*—Notaro & Michalos P.C.

(57) ABSTRACT

The invention relates to a method of improving the yield of a photobioreactor of the continuously operating recirculation type as a function of the species of micro-organism being cultured, of the thickness d of the chambers (10) of the reactor, and of the final concentration desired for the culture. In the method, transparent or respecting particles (15) are introduced into the reaction medium (11), which particles are of a density that is substantially equal to that of the reaction medium, thereby adjusting absorbance of the microorganism culture to optimum levels. The invention is mainly applicable to culturing phototropic micro-organisms.

5 Claims, 3 Drawing Sheets

METHOD FOR IMPROVING THE PERFORMANCE OF A PHOTOBIOREACTOR

This application is a 371 of PCT/FR98/02234, filed Oct. 19, 1998.

The invention relates to the field of photo-bioreactors, i.e. to devices that allow photosynthetic microorganisms to grow in controlled manner.

The invention relates more precisely to a method of improving the rate of growth of phototropic microorganisms in a culture in suspension in a liquid reaction medium, in which method the culture is subjected to a photosynthetic reaction activated by radiation passing through a transparent wall of a chamber of thickness d in a photobioreactor in which the reaction medium circulates.

It is known that the performance of systems for producing phototropic microorganisms vary depending on the species being cultured, and for a given species, they vary with concentration and with the thickness of the layer of culture that is subjected to radiation. Inter-specific variations are due to the fact that certain species suffer more than others in excess light, have better capacity to use low levels of light, and/or can be cultured at higher concentrations than others.

Variations in intraspecific performance are essentially associated with the thickness of the layer of culture subjected to radiation in the chamber and to the concentration of the culture. It has been observed that the absorbance or optical density of a microorganism in culture is more or less conserved regardless of the thickness d of the layer and the concentration c of the culture. This amounts to saying that d×c is equal to a constant expressed in terms of grams of microorganism dry weight per square meter of photosynthetic area, also known as density per unit area. The value of this constant lies in the range 10 grams per square meter ($g/m^2$) to 40 $g/m^2$ depending on species.

It can thus be seen that the average thickness d of chambers or pipes in which the photon reaction takes place ought to change with the species of microorganism being cultured for any desired concentration of the culture.

For a given species, and high concentration, the thickness d must be small, so as to make light accessible to the entire population of microorganisms in suspension in the liquid reaction medium circulating in the reactor chamber, in order to improve the yield of the reaction. However, too small a thickness d can give rise to serious head losses in the circuit.

It is always a good plan to increase the final concentration of microorganisms in the liquid reaction medium so as to limit the volumes of liquid that need to be processed upstream (preparing the nutritive medium) and downstream (concentrating biomass, treating the clarified medium before rejecting it). In order to improve the performance of bioreactors, it must therefore be possible to modify the thickness d of the chambers of the reactor as a function of the species being cultured. Unfortunately, this is not easily achieved in practice.

The object of the invention is to propose a method that is easy to implement and that makes it possible to adapt a given photobioreactor of the continuously operating recirculation type as a function of the micro-organism species being cultured and as a function of the concentration desired for the culture, regardless of the thickness d of the reactor chambers, so as to improve the rate of growth of the microorganisms.

The invention achieves this object by the fact that in the proposed method the absorbance of the culture is adjusted by adding transparent or reflecting particles to the reaction medium, which particles are of a density that is substantially equal to that of said reaction medium, the volume percentage occupied by said particles in the reaction medium being a function of the species of microorganism being cultured, of the thickness d of the chamber, and of the desired final concentration for the culture in the reaction medium.

The particles accompany the reaction medium in uniform manner in the flow. They have the effect of reducing optical path lengths within the chambers. Increasing the percentage per unit volume of particles in the reaction medium amounts to decreasing the thickness d of the layer in the chamber without increasing head losses, or to diluting the culture without adding water, where adding water would be undesirable from the point of view of collecting biomass.

Another expected effect of particles is that they will clean the optical walls of the reactor, and they will do so regardless of its shape.

The quantity of particles is a function in particular of the desired final concentration of biomass that is to be obtained. When a bioreactor operates continuously, this concentration remains constant. However, when starting a new culture and bringing the system up to full load, concentration is well below the desired final concentration. The microorganisms are then subjected to radiation at intensity that is too high, and that can harm yield.

According to another characteristic of the method of the invention, the turbidity of the reaction medium is measured and the intensity of the radiation is adjusted as a function of the measured turbidity.

Advantageously, the particles are compact in shape so as to avoid effects of lift and of superposition. The diameters of the circles escribed around the particles preferably lie in the range 0.5 millimeters (mm) to 10 mm. By way of example, particles are used that are made by coating hollow microbeads of glass in a transparent plastics material in proportions such that the density of the resulting composite is equal to that of the reaction medium.

The invention also relates to a photobioreactor of the continuously operating recirculation type for implementing the method of the invention.

The photobioreactor comprises: a closed loop in which it is possible to circulate a culture in suspension in a liquid reaction medium; at least one chamber of thickness d provided in said loop and defined by a transparent wall; means for emitting radiation through said transparent wall; means for introducing particles into said loop; and means for ensuring that said particles are retained within said loop.

Other advantages and characteristics of the invention will appear on reading the following description given by way of example and made with reference to the accompanying drawings, in which.

Figure 1:
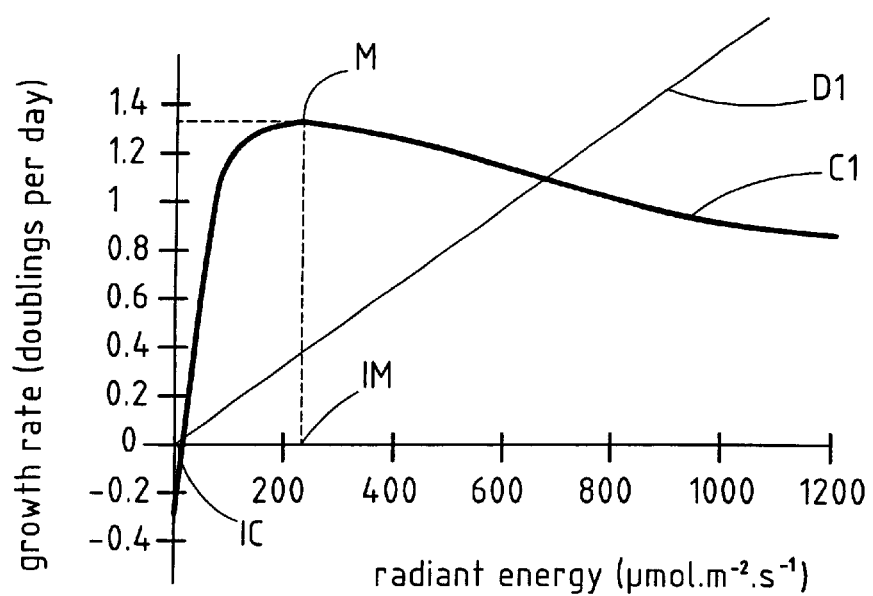
FIG. 1 is a graph plotting the growth of photo-tropic microorganisms of a given species as a function of the radiant energy of the radiation received in the reaction medium.

Phototropic organisms have the peculiarity of being sensitive to excess light as well as to insufficient light. In other words, whereas in physico-chemical processes the more photons injected into the reaction medium the better, when culturing phototropic micro-organisms, it is necessary to take care that the photons are supplied to the reaction within a narrow energy range. To illustrate this concept, reference is made to FIG. 1 which shows that the yield of a photosynthetic reaction as represented by curve C1 has a maximum M whereas the yield of a photochemical reaction, as represented by straight line D1 is approximately proportional to the available energy. The ordinate Gm of the point M corresponds to the maximum rate of growth for the culture. This rate is obtained at an optimum intensity of radiation Im. It can be seen that when this intensity of radiation is below Ic, then the population of microorganisms decreases. The constants Im, Ic, and Gm are obtained experimentally and are characteristic for each species of alga. When the intensity of radiation is greater than or less than Im, then the rate of growth is less than Gm. It can thus be seen that it is advantageous to ensure that the population of micro-organisms circulating in a photobioreactor is subjected therein to radiation at the optimum intensity Im characteristic of each species of alga.

The object of the invention is to adapt a photo-bioreactor of the continuously operating recirculation type as a function of the characteristics of different cultured organisms.

Figure 2:
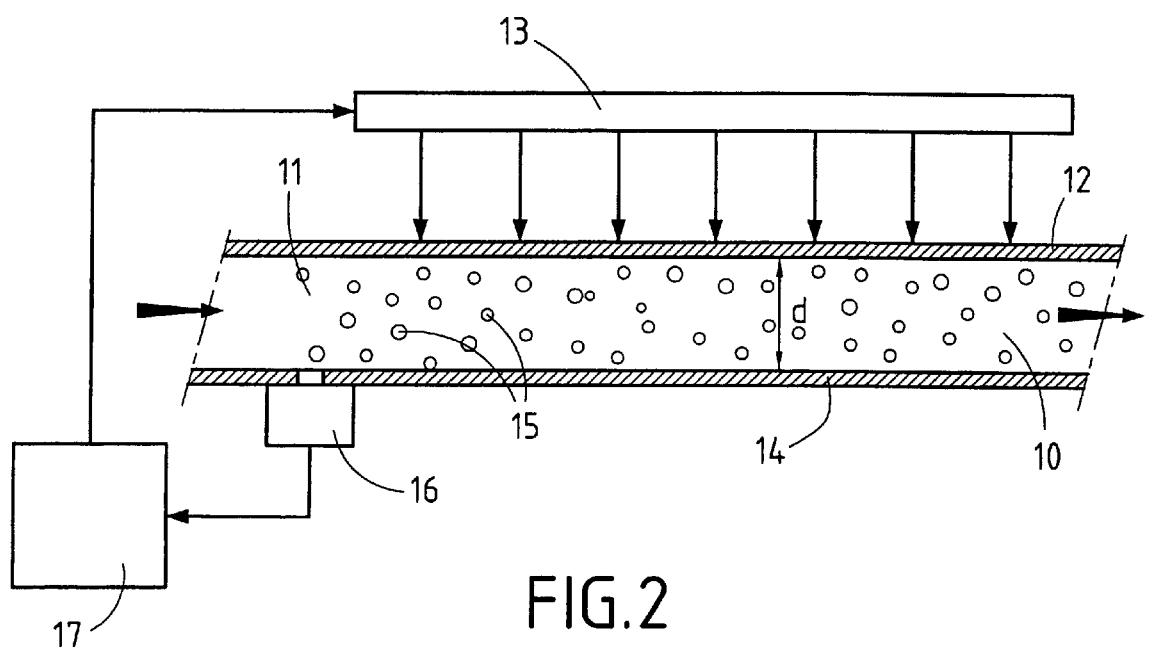
FIG. 2 is a diagram showing the method of the invention being implemented in a photobioreactor.

FIG. 2 is a diagram of a reactor for performing photosynthesis, the reactor comprising a chamber 10 in which a liquid reaction medium 11 circulates. One of the faces of the chamber is defined by a transparent wall 12 which receives radiation emitted by a light source 13, while its other face has a wall 14 that is lightproof. The walls 12 and 14 are spaced apart by a distance d. In order to make the light accessible to the population of microorganisms in suspension in the reaction medium 11, and in order to enable the concentration of the organisms in the reaction liquid to be high, particles 15 are introduced into the reaction medium 14. These particles 15 are transparent or reflective and of a density that is substantially equal to that of the reaction medium so as to accompany the medium uniformly as it circulates.

The volume percentage of particles 15 in the reaction medium is a function of the species of micro-organism being cultured, of the thickness d of the chamber 10, of the desired final concentration c of microorganisms in the reaction medium, and of the power of radiation from the light source 13 so as to ensure that the energy of the radiation is as close as possible to Im inside the chamber 10.

Reference 16 represents apparatus for measuring the turbidity of the reaction medium 11 and acting on apparatus 17 for adjusting the power of the radiation emitted by the light source 13.

When the concentration of microorganisms in the reaction medium 11 is below the desired final concentration for continuous production, the power of radiation from the light source is adapted by the adjustment apparatus 17 so as to obtain a maximum rate of growth.

This situation occurs in particular when a new culture is being started, i.e. while the reactor is coming up to full load.

The solid particles 15 can advantageously be made by coating hollow glass beads in a plastics material at proportions that are such that the density of the resulting composite is equal to that of the reaction medium. The plastics material is selected as a function of operating constraints. Polyester is particularly suitable since it retains its mechanical qualities over wide temperature ranges. The only restriction on the particles 15 is how they withstand temperature in the event of the reactor being sterilized initially by means of steam.

Figure 3:
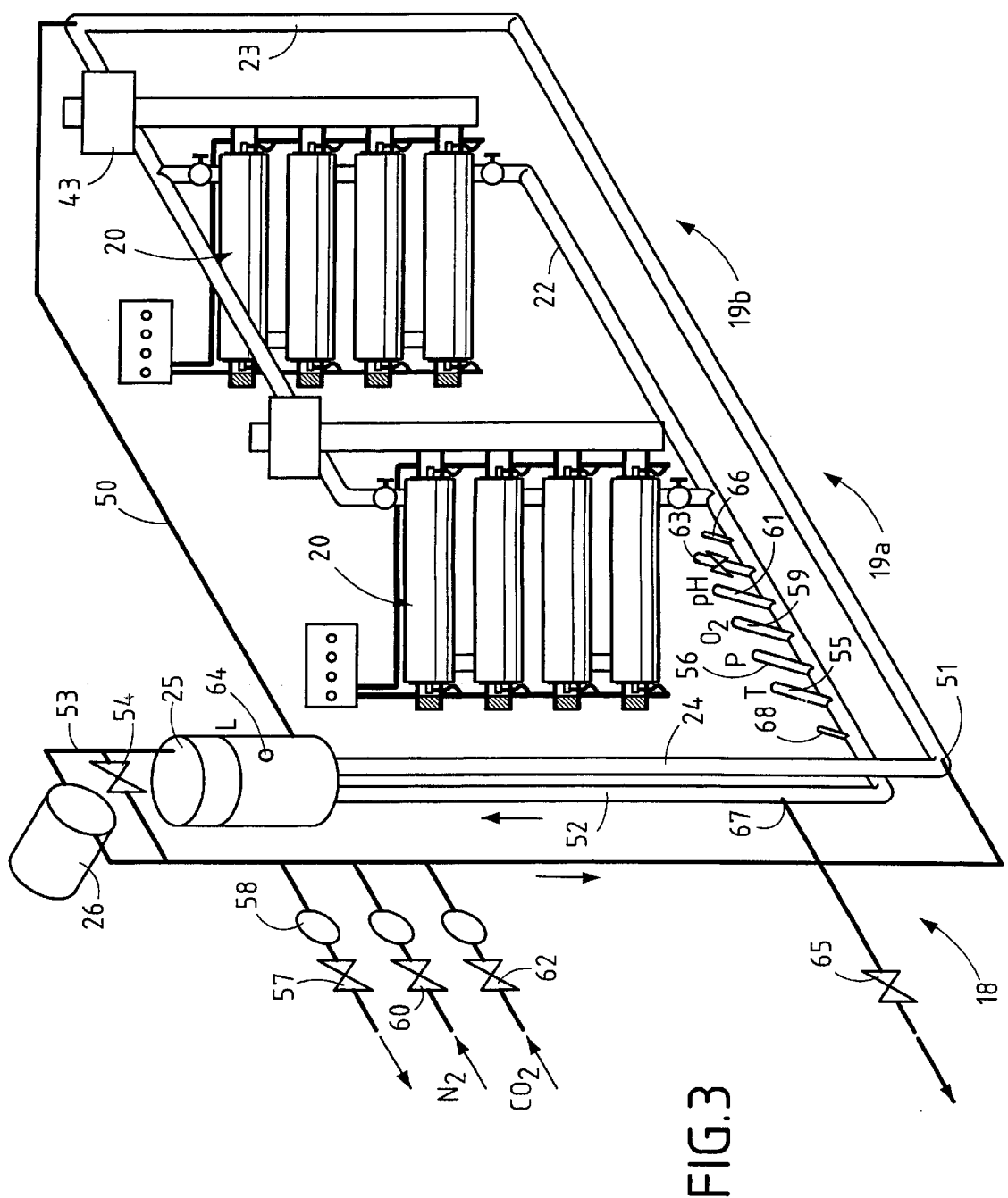
FIG. 3 is a perspective view of a photo-bioreactor for implementing the invention.
Figure 4:
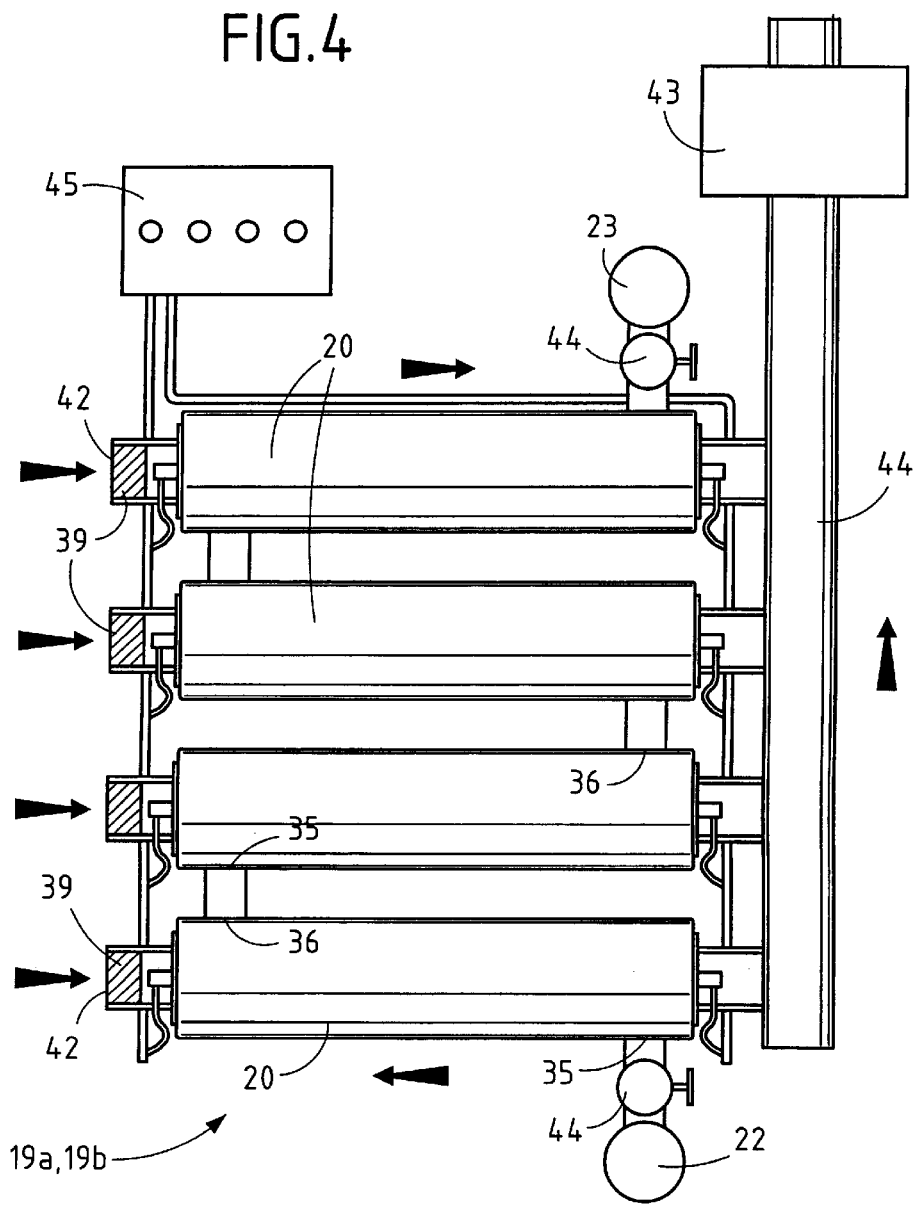
FIG. 4 shows a set of light chambers from the photo-bioreactor of FIG. 3.
Figure 5:
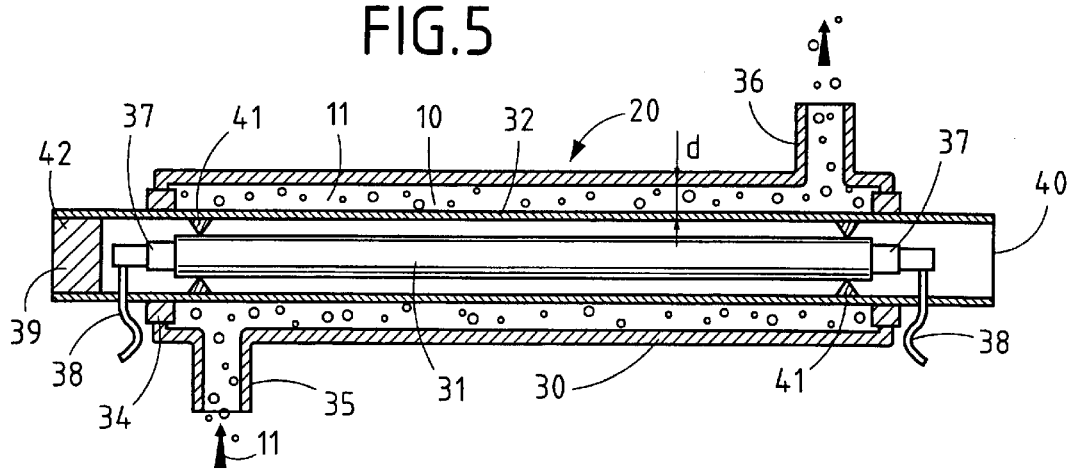
FIG. 5 is a vertical axial section through a light chamber of the FIG. 3 photobioreactor.

FIGS. 3 to 5 show a continuously operating recirculation type photobioreactor 18 adapted to implement the method of the invention.

This photobioreactor 18 comprises a plurality of sets 19a, 19b of light chambers 20 placed in parallel between a liquid reaction medium inlet manifold 22 and an outlet manifold 23. The outlet manifold 23 is connected to the bottom of a gas elevator 24 which leads to a tank 25 in which gas-liquid separation takes place.

The liquid returns to the inlet manifold 22 while the collected gas passes through a compressor 26 and is reinjected near the bottom of the vertical pipe of the elevator 24.

Each set 19a, 19b comprises a plurality of light chambers 20 placed one above another, and connected in series.

Each light chamber 20 comprises a cylinder 30 that is particularly closed at its ends with an artificial light source 31 being located in the center thereof, preferably a fluorescent tube which has the advantage of transforming electricity with high efficiency into visible light.

The fluorescent tube 31 is placed coaxially inside a transparent tube 32. Gaskets 34 provide sealing between the transparent tube 32 and the cylinder 30 at both ends thereof, so that the cavity or chamber 10 made in this way can receive a microorganism culture 11 that enters via an orifice 35 and that leaves via an orifice 36. These microorganisms thus receive the photon energy produced by the fluorescent tube 31 all along their path as they travel along the chamber 10.

The thickness d of the culture in register with the light source 31 is equal to the difference between the inside radius of the cylinder 30 and the outside radius of the transparent tube 32. This thickness is selected to be large enough to ensure that the energy is completely used up before reaching the wall of the cylinder 30. It lies in the range a few millimeters to a few centimeters. Nevertheless, it is possible to make a chamber 10 whose outside wall is reflective, e.g. out of stainless steel, thereby significantly increasing the length of the light path before complete extinction. It is also possible for the reflecting surface to be ground so as to make the reflected light isotropic and reduce radial reflection towards the transparent tube 32.

To increase the chances of all of the microorganisms receiving light, the culture flows along the chamber 10 under turbulent conditions.

Photosynthesis is accompanied by the production of oxygen, so care needs to be taken to ensure that the reaction medium 11 can escape via the outlet orifice 36 by placing the outlet orifice at the top. FIGS. 3 to 5 show that the chamber 10 is disposed horizontally. However other embodiments could have chambers that are vertical or sloping.

The connectors 37 of the fluorescent tubes 31 are connected to an electrical power supply via conductors 38 which pass through the transparent tube 32 or projections thereof so that its ends 39 and 40 are free. Each fluorescent tube 31 is centered in its transparent tube 32 by means of wedges 41. The diameter of the fluorescent tube 31 and the diameter of the transparent tube 32 are such that a passage is provided for air so as to enable both the fluorescent tube 31 and the culture to be cooled, with the culture being cooled by conduction through the transparent tube 32. In order to ensure that ambient dust does not become deposited on the optical surfaces due to the passage of air, it is advantageous for them to be held by means of a filter 42 disposed at the inlet end of the transparent tube 32. The other end 41 is connected to an extractor 43 (see FIG. 4) which serves to suck through the ambient air.

Since the fluorescent tubes 31 dissipate a large portion of the energy they consume in the form of heat, the culture would be subjected to a temperature rise if a cold source were not included in the loop. Since the optimum temperature for growth in photosynthetic micro-organisms is generally higher than the temperatures to be found in air-conditioned premises, the reactor can advantageously be placed in such premises where the air, conditioning system already in place serves to regulate the cold source while also ensuring comfort for operating personnel. The temperature of the culture is regulated by controlling the extractor 43.

FIG. 4 shows how a plurality of light chambers 20 can be assembled together to make up a set 19a, 19b, without the invention being limited in any way to that particular embodiment. Four light chambers 20 as described above are placed one above another and they are interconnected in series via their ends so that the culture follows a zigzag upward path from the inlet manifold 22 to the outlet manifold 23. The oxygen that is formed during photosynthesis is thus entrained into the top portion of the outlet manifold 23 without being given any chance to accumulate along this path.

As shown in FIG. 3, the inlet manifold 22 and the outlet manifold 23 can be connected to a plurality of, sets 19a, 19b. Valves 44 serve to isolate the sets 19a, 19b, thereby making them independent from one another. This is useful in particular when starting a culture, so as to enable the sets 19a, 19b to be put into operation progressively as a function of the concentration and the volume of inoculum, or in the event of one of the sets misfunctioning in operation.

Ambient air enters into the transparent tubes 32 via the ends 39 and the filters 42. Thereafter it is collected by a pipe 44 which is connected to the extractor 43. An electrical power supply 45 distributes electricity to the four fluorescent tubes in each set 19a, 19b.

As can be seen in FIG. 3, the two sets 19a, 19b are connected in parallel from bottom to top by the inlet manifold 22. The outlet manifold 23 takes the culture along a circuit for ensuring than the first set 19a does not receive preferential feed, and delivers it to the bottom of the gas elevator 24. A small-diameter pipe 50 connecting the top zone of the outlet manifold 23 to the tank 25 is intended to prevent oxygen accumulating in the top portion of the outlet manifold 23 since that would have the effect of reducing its flow section and of slowing down circulation of the reaction medium.

The function of the gas elevator 24 is to circulate the reaction medium. Compressed gas injected by the compressor 26 to the bottom 51 of the vertical column 24 has the effect of upwardly entraining the liquid contained in the column 24. Gas-liquid separation takes place in the tank 25 situated at the top of the column 24. The culture then returns to the inlet manifold 22 via a vertical pipe 52, while the gas is evacuated upwards via a pipe 53.

The gas is recycled in order to improve gas-liquid exchange, thereby reducing consumption to the strict minimum necessary for the reaction. For this purpose, the collected gas passes via the compressor 26 and is reinjected into the bottom 51 of the column 54 of the gas elevator. A branch connection allows the flow rate of the injected gas to be adjusted by acting on a valve 54.

The various regulations that occur within the above-described photobioreactor 18 are described below. For reasons of clarity, the regulator units are not shown in the drawings and the sensors are not shown in detail.

The sensor 55 for sensing temperature T serves to control the operation of the air extractors 43 in each of the sets 19a, 19b.

The effect of injecting gas to the bottom 51 of the gas elevator 24 is to increase pressure within the confinement. Regulating pressure to a value that is above ambient by more than 0.1 bars has the purpose of ensuring that in the event of a leak, exchange between the outside and the inside of the confinement does not take place, since that might contaminate the culture. A sensor 56 for sensing pressure P controls the opening of the valve 57, thereby allowing gas contained in the reactor to escape; A filter 58 having a cutoff at 0.22 microns ($\mu$m) serves to avoid backflow contamination.

Oxygen accumulation within the confinement is harmful to the culture and must be controlled. For this purpose, oxygen is moved by injecting air or nitrogen into the gas circuit, so that oxygen concentration does not exceed a threshold lying in the range one to three times saturation. In the embodiment of FIG. 3, a sensor 59 for sensing oxygen $O_2$ controls opening of a solenoid valve 60 which has the effect of allowing nitrogen to enter into the gas circuit of the reactor. The nitrogen is initially passed through a filter having a 0.22 $\mu$m cutoff so as to avoid contaminating the reaction medium.

Carbon dioxide is the most common source of carbon for photosynthesis. It is injected into the gas circuit such that the pH of the culture (which pH is influenced by $CO_2$ and tends to increase under the effect of photosynthesis) is kept constant and equal to values lying, in the range 6 to 8 depending on the species in culture. For this purpose, a sensor 61 sensing pH controls opening of a solenoid valve 62 which has the effect of allowing carbon dioxide to enter into the gas circuit of the reactor. It passes initially through a filter having a 0.22 $\mu$m cutoff, thus making it possible to avoid contaminating the reaction medium.

New nutrient medium is injected into the reactor via a pipe 63. This injection causes the level in the tan 25 placed above the gas elevator 24 to rise. This level must be regulated since otherwise there would be a danger of liquid becoming sucked into the compressor 26 and giving rise to various kinds of damage. For this purpose, a detector 64 monitors level L and controls the opening of a takeoff solenoid valve 65.

In addition, means 66 are provided in the inlet manifold 22 for introducing particles 15 into the liquid reaction medium, or for withdrawing them. In order to prevent particles 15 being entrained out from the reactor when culture is drawn off, a screen of mesh size slightly smaller than the size of the particles 15 is placed in the connection 67.

A turbidity detector 68 having a threshold controls metering pumps for injecting new nutrient medium when the culture reaches a certain concentration. The turbidity detector can also act on the power of the fluorescent tubes 31 when the concentration of the microorganisms is below the desired concentration.

These various kinds of regulation operate without interfering mutually and they suffice to automate the reactor during ordinary operation.

However, initial sterilization of the photo-bioreactor 18 and initial introduction of inoculum require manual operations that are difficult to automate.

What is claimed is:

1. A method for improving a rate of growth of phototropic microorganisms in a culture in suspension in a liquid reaction medium circulating in a chamber of a photobioreactor, said chamber having a transparent wall through which pass radiation for activating the photosynthesis reaction of the phototropic microorganisms, the method comprising:

adding transparent or reflecting particles to the reaction medium in order to adjust radiation absorbance of the culture, the density of said particles being substantially equal to the density of the medium; and the volume percentage of said particles in the reaction medium being a function of the species of microorganism in the culture, the thickness of the chamber that corresponds to an optical path of the radiation, and the desired final concentration of the culture in the reaction medium.

2. A method according to claim 1, in which the reaction medium is circulated in a closed circuit, an inoculum is introduced into said closed circuit, and a portion of the reaction medium is extracted once the concentration of the culture has reached the desired threshold, the method including measuring the turbidity of the reaction medium and adjusting the intensity of the radiation as a function of the measured turbidity.

3. A method according to claim 1, wherein the particles are compact in shape so as to avoid effects of lift and of superposition.

4. A method according to claim 1, wherein the particles have a diameter in the range of 0.5 mm to 10 mm.

5. A method according to claim 1, wherein the particles used are made by coating hollow glass microbeads in a transparent plastics material at proportions such that the density of the resulting composite is equal to that of the reaction medium.

* * * * *